US006953866B2

United States Patent
Malz, Jr. et al.

(10) Patent No.: US 6,953,866 B2
(45) Date of Patent: Oct. 11, 2005

(54) PROCESS FOR PREPARING ORTHO SUBSTITUTED PHENYLAMINES

(75) Inventors: Russell E. Malz, Jr., Glastonbury, CT (US); Ranjit Kumar, Storrs, CT (US); Luis Javier Garces, Storrs, CT (US); Steven L. Suib, Storrs, CT (US)

(73) Assignee: Crompton Corporation, Middlebury, CT (US)

( * ) Notice: Subject to any disclaimer, the term of this patent is extended or adjusted under 35 U.S.C. 154(b) by 0 days.

(21) Appl. No.: 10/769,365

(22) Filed: Jan. 30, 2004

(65) Prior Publication Data

US 2004/0162444 A1 Aug. 19, 2004

Related U.S. Application Data

(60) Provisional application No. 60/445,680, filed on Feb. 6, 2003.

(51) Int. Cl.⁷ .................. C07C 209/18; C07C 209/02
(52) U.S. Cl. ............................................ 564/402
(58) Field of Search .......................... 564/402

(56) References Cited

U.S. PATENT DOCUMENTS

| | | | | |
|---|---|---|---|---|
| 2,714,614 A | * | 8/1955 | Weinmayr | 564/395 |
| 5,574,187 A | | 11/1996 | Malz et al. | 564/402 |
| 5,689,007 A | | 11/1997 | Malz et al. | 564/402 |

OTHER PUBLICATIONS

Heller et al., NATURE, A New View of the Arylhydroxylamine Rearrangement, vol. 168, pp. 909–910, (1951).

Bamberger, Justin Liebig's Annalen der Chemie, vol. 390, pp. 139–144 (1912): ibid., 243–245, 294–296.

Smith et al., Catalysis of Organic Reactions, vol. 68, Marcel Dekker, New York, pp. 335–342, (1996).

Gerard V. Smith et al. "A New Route to P–aminodlphenylamine via Condensation of Aniline with either Phenihydroxylamine or Nitrosobenzene". Catalysis of Organic Reactions. vol. 68 (1996) XP001152157.

XP002291261: Database Crossfire Beilstein. Beilstein Institut zur Foerderung der Chemischen Wissenschaften. Frankfurt. vol. 31. p. 1506 (1898).

XP002291262: Database Crossfire Beilstein. Beilstein Institut zur Foederung der Chemischen Wissenschaften. Frankfurt. vol. 35. p. 3706 (1902).

XP002291263: Database Crossfire Beilstein. Beilstein Institut zur Foederung der Chemischen Wissenschaften. Frankfurt. vol. 31. p. 1506 (1898).

XP002291264: Database Crossfire Beilstein. Beilstein Institut zur Foederung der Chemischen Wissenschaften. vol. 17. pp. 710–713 (1981).

* cited by examiner

*Primary Examiner*—Brian Davis
(74) *Attorney, Agent, or Firm*—Daniel Reitenbach

(57) ABSTRACT

A process is disclosed for preparing ortho substituted phenylamines comprising contacting phenylhydroxylamine, optionally substituted with at least one inert substituent, with a nucleophilic reagent in the presence of a manganese oxide at a temperature between about 10° C. and about 170° C. and a pressure from subatmospheric to superatmospheric such that an ortho substituted phenylamine, optionally correspondingly substituted with at least one inert substituent, is predominantly formed.

14 Claims, No Drawings

PROCESS FOR PREPARING ORTHO SUBSTITUTED PHENYLAMINES

I claim the benefit under Title 35, United States Code, § 120 to U.S. Provisional Application No. 60/445,680 filed Feb. 6, 2003 entitled PROCESS FOR PREPARING ORTHO SUBSTITUTED PHENYLAMINES.

BACKGROUND OF THE INVENTION

1. Field of the Invention

This invention relates to the preparation of ortho substituted phenylamines from phenyl-hydroxylamine and nucleophilic reagents, such as amines and alcohols. o-Phenylenediamines, and more specifically, o-aminodiphenylamine are illustrative of the ortho substituted phenylamines formed in this invention.

2. Description of Related Art

Ortho substituted phenylamines find a variety of utilities depending upon the ortho substituent. They are used, inter alia: in dye formulations; as intermediates in electrolyte compositions; to generate photosensitive compounds; as lubricant antioxidants, viscosity improvers, and dispersants; to generate scale disposition preventers; as intermediates in thermal transfer agents; and to generate adhesives.

The syntheses of ortho substituted phenylamines vary depending upon the ortho substituent and often require several steps, which add undesirably to production costs.

It is known that phenylhydroxylamine reacts with nucleophilic reagents in the presence of aqueous inorganic acids to yield p-substituted phenylamines. See, for example, Heller, H. E. et al., *Nature,* 168:909 (1951) and Bamberger, E., *Justin Liebig's Annalen der Chemie,* 390, 139–144 (1912): Ibid., 424, 243–245, 294–296 (1921). It is disclosed that phenylhydroxylamine is converted to p-hydroxyaniline in the presence of dilute sulfuric acid. It is further taught that phenylhydroxylamine reacts with aniline in the presence of dilute sulfuric acid to yield p-aminodiphenylamine. It is also disclosed that phenylhydroxylamine is converted to ortho and p-chloroaniline when the acid employed is hydrochloric acid. Disadvantageously, Bamberger describes multiple by-products, including benzadiene, azoxybenzene and aniline. In a practical sense, there is an added disadvantage in that separation of the acid from the product stream can be expensive. The acid must be neutralized creating a waste stream, which must be disposed of.

It is known that reacting phenylhydroxylamine with aniline in the presence of a homogeneous acid catalyst or a solid acid catalyst can lead to p-aminodiphenylamine. See, for example, Smith, G. V. et al., *Catalysis of Organic Reactions,* Vol. 68, Marcel Dekker, New York (1996) pp. 335–342.

It is disclosed that phenylhydroxylamine and aniline in the presence of concentrated HCl, HZSM-5, HY zeolites, Nafion, filtrol (acid clay), $NaHSO_4/SiO_4$, or montmorillonite yield p-aminodiphenylamine. In each case, the predominant isomer of aminodiphenylamine was the para isomer.

U.S. Pat. Nos. 5,574,187 and 5,689,007 disclose processes of preparing para substituted phenylamines, such as, p-phenylenediamines, and particularly, p-aminodiphenylamine. One process involves contacting phenylhydroxylamine with a nucleophilic reagent, such as aniline, in specified proportions and within a specified temperature range, in the absence of oxygen, and in the presence of a homogeneous acid catalyst, such as hydrochloric acid. A second process involves contacting phenylhydroxylamine with a nucleophilic reagent, such as aniline, in the presence of a solid acid catalyst, such as acidic zeolite Y, under reaction conditions.

SUMMARY OF THE INVENTION

The present invention is directed to a process for preparing mixtures of substituted phenylamines in which the predominant isomer is the ortho isomer. The process involves contracting phenylhydroxylamine with aniline in the presence of a manganese oxide octahedral molecular sieve (K-OMS-2) that has been converted to the $H^+$ form by successive ion exchanges with $HNO_3$. Advantageously, this process produces a very high selectivity to the ortho isomer. Moreover, the catalyst used in this process, H-K-OMS-2, is heterogeneous and, therefore, the ortho substituted aminodiphenylamine is easily and inexpensively separated from the catalyst. More advantageously, in preferred embodiments of this invention, the process produces ortho substituted phenylamines in good yield.

More particularly, the present invention is directed to a process for preparing ortho substituted phenylamines comprising contacting phenylhydroxylamine, optionally substituted with at least one inert substituent, with a nucleophilic reagent in the presence of a manganese oxide at a temperature between about 10° C. and about 170° C. and a pressure from subatmospheric to superatmospheric such that an ortho substituted phenylamine, optionally correspondingly substituted with at least one inert substituent, is predominantly formed.

In another aspect, the present invention is directed to a process for preparing ortho substituted phenylamines comprising contracting phenylhydroxylamine, optionally substituted with at least one inert substituent, with a nucleophilic reagent, the molar ratio of nucleophilic reagent to phenylhydroxylamine ranging from about 2 to about 100, the contacting of the phenylhydroxylamine and nucleophilic reagent being conducted in the absence of oxygen and in the presence of a catalyst that is a cryptomelane-type manganese oxide Octahedral Molecular Sieve (K-OMS-2), with a composition of $KMn_8O_{16} \cdot nH_2O$ (n=0.5–10) in which the K-OMS-2 comprises $MnO_6$ octahedral structural units that are edge and corner shared to form a 4.6×4.6 tunnels as a result of 2×2 arrangement of octahedra, in which the potassium ions are present in the tunnels with a small amount of water and said potassium ions are exchanged by $H^+$ ions by ion-exchanging K-OMS-2 with nitric acid to obtain the acidic form of K-OMS-2 (H-K-OMS-2) at temperatures ranging from about 70° C. to about 120° C., whereby the optionally-substituted ortho substituted phenylamine is formed in amounts equal to or greater than the para phenylamine.

DESCRIPTION OF THE PREFERRED EMBODIMENTS

In accordance with the present invention, phenylhydroxylamine is contacted with aniline in the presence of a manganese oxide octahedral molecular sieve (K-OMS-2) that has been converted to the $H^+$ form by successive ion-exchanges with $HNO_3$ (H-K-OMS-2) to yield ortho substituted phenylamines.

Alternatively, phenylhydroxylamine substituted with at least one inert substituent can replace unsubstituted phenylhydroxylamine in the process of the invention such that the correspondingly inertly substituted derivative of an ortho substituted phenylamine is formed.

In a preferred embodiment, phenylhydroxylamine is contacted with aniline or a substituted aniline in the presence of the aforementioned catalysts to yield o-aminodiphenylamine.

Phenylhydroxylamines that are suitable for use in the process of this invention include unsubstituted phenylhydroxylamine and substituted phenylhydroxylamines, provided the substituent(s) of such substituted phenylhydroxylamines is (are) inert with respect to the process of the invention. In addition, any inert substitutents should preferably be located at positions other than the ortho substituent positions relative to the hydroxylamine moiety. At least one of the ortho positions must remain unsubstituted since that is the position that is involved in the process with the nucleophilic reagent.

Suitable inert substituents include linear and branched $C_1$–$C_{10}$ alkyl moieties, amino (—$NH_2$), hydroxyl, halo, keto (—C(O)R), ether (—OR), and ester (—OC(O)R) moieties wherein the R substituent is preferably a $C_1$–$C_{10}$ alkyl or a $C_6$–$C_{10}$ aryl or alkaryl group. Non-limiting examples of suitable substituted phenylhydroxylamines include methyphenylhydroxylamine, ethylphenylhydroxylamine, isopropylphenylhydroxylamine, aminophenylhydroxylamine, hydroxyphenylhydroxylamine and the like.

Preferably, the phenylhydroxylamine is unsubstituted or substituted with a $C_1$–$C_{10}$ alkyl moiety. More preferably, the phenylhydroxylamine is unsubstituted phenylhydroxylamine.

A nucleophilic reagent is also required for the process of this invention. The term "nucleophilic reagent" is meant to include ions or molecules that are capable of donating a pair of electrons to an atomic nucleus, so as to form a covalent bond. Suitable nucleophiles include ammonia, water, aliphatic alcohols, phenols, halides in the acid or tetralkylammonium forms, and primary and secondary aliphatic amines, alicyclic amines and aryl and alkaryl amines. Preferred amines are represented by the formula $R'_2NH$, wherein each R' is independently selected from the group consisting of hydrogen, $C_1$–$C_{20}$ aliphatic moieties, $C_4$–$C_8$ alicyclic moieties, and $C_6$–$C_{15}$ aryl or alkaryl moieties. Non-limiting examples include ethylamine, diethylamine, propylamine, dipropylamine, butylamine, dibutylamine, and analogous higher homologues.

Suitable examples of alicyclic amines include cyclopentylamine and cyclohexylamine. Suitable examples of aryl and alkaryl amines include aniline toluidine, dimethylaniline, ethylphenylamine, propylphenylamine, and isopropylphenylamine. Preferred aliphatic alcohols include ethanol, propanol, isopropanol, butanols, pentanols, hexanols, heptanols, octanols, and higher homologues of these. Suitable phenols include phenol and $C_1$–$C_{10}$ alkyl substituted phenols, such as cresol.

Suitable halides include tetraalkylammonium chlorides, bromides, and iodides, such as tetraethylammonium bromide and tetramethylammonium chloride, as well as the hydrogen halides, such as hydrogen chloride, hydrogen bromide, hydrogen iodide, and hydrogen fluoride. The preferred nucleophilic reagents are amines of the formula $R'_2NH$ wherein each R' is independently selected from the group consisting of hydrogen, $C_1$–$C_{20}$ aliphatic moieties, $C_4$–$C_8$ alicyclic moieties, and $C_6$–$C_{15}$ aryl or alkaryl moieties.

More preferred nucleophilic reagents are amines of the formula $R'_2NH$ wherein each R' is independently selected from the group consisting of hydrogen, $C_1$–$C_5$ alkyl moieties, and $C_6$–$C_{10}$ phenyl or alkyl-substituted phenyl moieties. The most preferred nucleophilic reagent is aniline.

Any molar ratio of nucleophilic reagent to phenylhydroxylamine is suitable for use in the practice of the present invention provided the desired ortho substituted phenylamine is obtained as a product. When the nucleophilic reagent is a liquid under the process conditions, the nucleophilic reagent may act as the solvent for the process. Consequently, the amount of nucleophilic reagent employed relative to the phenylhydroxylamine is generally large. Suitable molar ratios of nucleophilic reagent employed relative to phenylhydroxylamine are generally greater than or equal to 2. Preferably, the molar ratio of nucleophilic reagent to phenylhydroxylamine ranges from about 2 to about 100. When a solid acid catalyst is employed in the process of this invention, the most preferred molar ratio of nucleophilic reagent to phenylhydroxylamine lies in the range of from 3 and 20. Alternatively, if the nucleophilic reagent is a solid, it may be desirable to conduct the process in the presence of an inert solvent. The term "inert" means the solvent does not interfere with the process of this invention and is unreactive towards the reagents, products, and catalysts.

Suitable solvents include polar organic solvents, such as dimethylsulfoxide, dimethylacetamide, and nitrobenzene. If a solvent is employed, the quantity can vary depending on the solubilities of the specified reagents and products involved. One skilled in the art can readily determine an acceptable quantity of solvent. As a general rule, the ratio of moles of solvent to moles of phenylhydroxylamine is greater than 5, but less than about 20, and is preferably in the range of from about 8 to about 12.

The catalyst employed in the practice of the present invention is K-OMS-2, a cryptomelane-type manganese oxide Octahedral Molecular Sieve, with a composition of $KMn_8O_{16} \cdot nH_2O$ (n=0.5–10). K-OMS-2 comprises $MnO_6$ octahedral structural units that are edge and corner shared to form 4.6×4.6 tunnels as a result of a 2×2 arrangement of octahedra. Potassium ions are present in the tunnels along with a small amount of water. $K^+$ ions are exchanged for $H^+$ ions by ion-exchanging K-OMS-2 with $HNO_3$ to obtain the acidic form of K-OMS-2.

Synthesis of H-K-OMS-2

A quantity of 11.57 grams (58.5 mmol) of $MnCl_2 \cdot 4H_2O$ is placed in a flask and 34 mL of doubly distilled water (DDW) is added to it (Solution A). Another solution of 6.95 grams (44.0 mmol) of $KMnO_4$ in 112.5 grams of DDW and 3.4 mL of concentrated $HNO_3$ is prepared in a beaker and added drop wise under vigorous stirring to solution A. It is then refluxed for 16 hours at 100° C. The product is then filtered and washed several times with DDW. The product (K-OMS-2) is dried at 120° C. for 12 hours and then calcined at 280° C. for six hours.

Ion-Exchange:
 (i) With 1M $HNO_3$:
 Two grams of K-OMS-2 was combined with 50 mL of 1M $HNO_3$. The mixture was stirred vigorously and kept at 80° C. for 6 hours. The product was filtered and washed several times with DDW. This process was repeated 4 times. The final product was filtered and washed several times with DDW. The product (H-K-OMS-2) was dried at 120° C. for 12 hours and then calcined at 280° C. for 6 hours.
 (ii) With Concentrated $HNO_3$:
 The same procedure as above is repeated with concentrated $HNO_3$. K-OMS-2 was exchanged with conc. $HNO_3$ two times.

Other suitable catalysts include all other types of manganese oxide materials, such as OMS-1(3×3), OMS-4 (1×2), OMS-5 (2×4) and OL-1 (layered manganese oxide).

The process of the present invention can be conducted in any standard reactor, such as a stirred batch reactor, a fixed-bed continuous flow reactor, a fluidized bed reactor, or a transport reactor. Typically, the phenylhydroxylamine is in the liquid phase and the nucleophilic reagent is in the liquid or gaseous phase, preferably, the liquid phase. Usually, air is excluded from the reactor by flushing or pressurization with a non-reactive gas, such as nitrogen, helium, argon, or hydrogen. The presence of air leads to lower yields.

Any operating conditions may be employed provided the desired ortho substituted product is formed. Preferred operating conditions vary depending upon the particular phenylhydroxylamine, the particular nucleophile, and the concentrations of these materials. Usually, the process temperature ranges from about 10° C. to about 170° C., preferably from about 70° C. to about 120° C., more preferably from about 90° C. to about 110° C. In a batch reactor, reaction time to nearly complete conversion of the phenylhydroxylamine is typically about three hours or less. In a fixed-bed, continuous-flow reactor, the pressure can vary from below atmospheric to superatmospheric, but is preferably slightly superatmospheric, for example, from about 1.5 to about 5.0 atmospheres, so as to exclude air from leaking into the reactor.

The quantity of solid acid catalyst employed in the process of the present invention can range from a catalytic amount to more than a stoichiometric amount relative to the phenylhydroxylamine, provided the desired ortho phenylamine product is formed. In a batch reactor, the catalyst is employed in an amount ranging from about 0.1 to about 20 parts per 1 part by weight relative to the phenylhydroxylamine; preferably, from about 0.5 to about 15 parts by weight per 1 part by weight relative to the phenylhydroxylamine. In a continuous fixed-bed reactor, the weight hourly space velocity (WHSV) determines the ratio of reactants to catalyst as well as the residence time of the reagents in the reactor.

As employed herein, the WHSV is defined as grams of feedstream per grams of catalyst per hour or simply $hr^{-1}$. It ranges from about 0.01 $hr^{-1}$ to about 100 $hr^{-1}$.

When phenylhydroxylamine, optionally substituted with at least one inert substituent, is contacted with a nucleophilic reagent in the presence of a solid acid catalyst, an ortho substituted phenylamine is produced. The product may be represented by the formula:

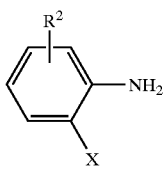

wherein $R^2$ is hydrogen, or alternatively can represent one or more inert substituents mentioned hereinbefore in connection with the phenylhydroxylamine reactant; and the X is hydroxyl, halo, alkoxy, phenoxyl or amino of the formula —$NR'_2$, wherein each R' is independently hydrogen, a $C_1$–$C_{20}$ aliphatic, $C_4$–$C_8$ alicyclic, or a $C_6$–$C_{15}$ aryl or alkaryl moiety. Preferably, X is amino of the formula —$NR'_2$, wherein each R' is independently hydrogen, a $C_1$–$C_{20}$ aliphatic, $C_4$–$C_8$ alicyclic, or a $C_6$–$C_{15}$ aryl or alkaryl moiety and the product is classified as an o-phenylenediamine. More preferably, X is amino wherein R' is independently hydrogen, a $C_1$–$C_5$ alkyl, or a $C_6$–$C_{10}$ phenyl or alkyl-substituted phenyl moiety. Most preferably, $R^2$ is hydrogen, X is —$NR'_2$, one R' is hydrogen, the other R' is phenyl, and the product is o-aminodiphenylamine represented by the formula:

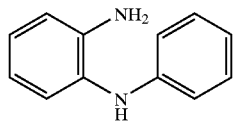

For purposes of this invention, the ratio of the ortho to para products generated refers to the area percent HPLC ratio as determined in reference to authentic samples.

Various features and aspects of the present invention are illustrated further in the examples that follow. While these examples are presented to show one skilled in the art how to operate within the scope of the invention, they are not intended in any way to serve as a limitation upon the scope of the invention. All percentages are in area percent.

EXAMPLES

TABLE 1

Acid Catalyst giving a Para to Ortho Ratio of ≧ 1:1[a]

| Example # | Catalyst Type | Weight (grams) | Temperature (° C.) | Ratio of para:ortho |
|---|---|---|---|---|
| 1[b] | Concentrated HCl | ~3 | 100 | No ortho detected |
| 26[d] | ITQ6(3).HCl | 0.10 | 110 | 4:1 |
| 14[b] | Aniline Hydrochloride | 0.10 | 140 | 3.5:1 |
| 11[d,k] | ITQ6(2) | 0.10 | 110 (1 h) | 3.4:1 |
| 7[b,e] | Concentrated HCl | ~1 | 100 | 3:1 |
| 16[d] | Aniline Hydrochloride | 0.010 | 110 | 3:1 |
| 10[c] | ITQ2(1) | 0.10 | 110 | 3:1 |
| 23[d,l,k] | ITQ6(2) | 0.10 | 110 | 3:1 |
| 24[d] | ITQ6(2).HCl | 0.10 | 110 | 2.6:1 |
| 25[d,j] | ITQ6(3) | 0.10 | 110 | 2.5:1 |
| 29[d] | ITQ2.HCl | 0.10 | 110 | 2.5:1 |
| 12[c] | H-CHA | 0.10 | 140 | 2.5:1 |
| 19[d] | Ca-Montmorillonite (SM1502A) | 0.10 | 80 | 2.3:1 |
| 11[d,k] | ITQ6(2) | 0.10 | 120 (1 h) | 2.1:1 |
| 15[d] | ITQ6(2) | 0.10 | 140 | 2:1 |
| 27[d,k] | ITQ6(3) | 0.20 | 160 | 2:1 |
| 20[d,g] | ITQ2(1) | 0.10 | 140 | 2:1 |
| 28[d] | ITQ6(3).HCl | 0.50 | 160 | 2:1 |
| 8[b] | MCM-41 | 0.050 | 140 | 2:1 |
| 2[b] | H-RHO (11-1) | 0.10 | 140 | 2:1 |
| 3[b] | H-RHO (11-1) | 0.10 | 140 | 2:1 |
| 5[b] | H-RHO (GG) | 0.10 | 140 | 2:1 |
| 6[b] | H-RHO (9-2) | 0.10 | 140 | 2:1 |
| 33[d] | H-ZSM5 | 0.20 | 140 | 2:1 |
| 11[c] | H-MER | 0.10 | 140 | 2:1 |
| 31[d] | H-ZSM-23 | 0.20 | 140 | 1.8:1 |
| 22[d,h]** | H-K-OMS-2 (Exchanged once with 1 M HNO₃) | 0.10 | 140 | 1.5:1 |
| 13[c] | H-LTL | 0.10 | 140 | 1.5:1 |
| 11[d,k] | ITQ6(2)* | 0.10 | 90 (2 h) | 1.5:1 |
| 11[d,k] | ITQ6(2)* | 0.10 | 100 (1 h) | 1.4:1 |
| 9[b] | Sulfated Zirconia | 0.10 | 140 | 1:1 |
| 12[c] | H-rho | 0.10 | 110 (3 h) | 1:1 |
| 13[c] | H-rho | 0.10 | 80 (20 h) | 1:1 |

**Comparative example.
ITQ-6 is a delaminated zeolite material, which was prepared as described by Corma, A. et al., J. Am. Chem. Soc. 122: 2804–2809 (2000).
ITQ-2 is a delaminated zeolite material, which was prepared as described by Corma, A. et al., Nature 396: 353 (1998).
MCM-41 is a mesoporous material having pores greater than 20 Å and smaller than 500 Å, which was prepared as described by Franke, O. et al., Studies in Surface Science and Catalysis 91(Preparation of Catalysts VI): 309 (1995).

TABLE 1-continued

Acid Catalyst giving a Para to Ortho Ratio of ≥ 1:1[a]

| Example # | Type | Catalyst Weight (grams) | Temperature (° C.) | Ratio of para:ortho |
|---|---|---|---|---|

H-rho is a small pore size zeolite having a pore size around 4 to 5 Å, which was prepared as described by Robson, H. et al., Molecular Sieves Advances in Chemistry Series, Am. Chem. Soc. 12: 106 (1973). Descriptions of other catalysts in Table 1 can be found in Chen, C.Y., et al., Microporous Mat. 2(1): 17 (1993).

FOOTNOTES TO TABLE 1

[a]Phenylhydroxylamine (PHA, 0.10 gram) was dissolved in 5.1 grams (55 mmol) of aniline and loaded into a Sage syringe pump. This was then pumped into a 3-neck round bottom flask of the size indicated in the footnotes. The three neck flask is equipped with three septum. One septum is pierced with two long needles to allow sub surface delivery. The first delivers liquid from the syringe pump. The second delivers a nitrogen purge. The second septum is pierced with a temperature measuring device. The third septum is pierced with a short needle to allow nitrogen venting. This flask, which contained 55.1 grams (55 mmole) of aniline, was heated to the indicated temperature. The PHA in aniline was pumped in over two hours. The reaction was cooled and the reaction mixture analyzed by HPLC. As determined by area % HPLC analysis using a Beckman System Gold HPLC equipped with a Zorbax column (8.0 cm × 4.5 mm) and a variable wavelength detector using a wavelength of 290 nm. The eluent was water with 0.05 M ammonium acetate and acetic acid (pH 5.0 ± 0.3) and acetonitrile.
[b]Used a 250-mL round bottom flask.
[c]Used a 50-mL round bottom flask.
[d]Used a 25-mL round bottom flask.
[e]The ratio of HCl:PHA: ~200:1. The ratio of Aniline:HCl: ~3:1.
[f]The ratio of HCl:PHA: ~70:1.
[g]Same as a, but the PHA in aniline was added at once.
[h]The same procedure as footnote a except the PHA in aniline was added over a period of 35 minutes.
[i]Si/Al = 3.7:1 (Batch Composition)
[j]Si/Al = 4:1 (Batch Composition)
[k]These are all part of Example 11, which was run at 90° C. for two hours with a sample taken every hour.

TABLE 2

Effect of Catalyst Exchange on selectivity[a]

| Type | Catalyst Weight (grams) | Temperature (° C.) | Ratio of para:ortho[c] |
|---|---|---|---|
| K-OMS-2[b] | 0.10 | 140 | No Reaction |
| H-K-OMS-2 (1) (Exchanged once with 1 M HNO$_3$)[b] | 0.10 | 140 | 1.5:1 |
| H-K-OMS-2 (2) (Exchanged twice with 1 M HNO$_3$) | 0.20 | 140 | 1:5.3 |
| H-K-OMS-2 (4) (Exchanged four times with 1 M HNO$_3$) | 0.20 | 120 | 1:16.2 |
| H-K-OMS-2 (2C) (Exchanged twice with concentrated HNO$_3$) | 0.20 | 120 | 1:23.2 |

FOOTNOTES TO TABLE 2

[a]Aniline (5.11 grams, 54.9 mmol) and the indicated weight of the indicated catalyst were placed in a 25 mL 3-neck round bottom flask fitted with a reflux condenser, thermometer, and magnetic stirrer. The flask was purged with N$_2$ gas for an hour and heated to 120° C. PHA (0.10 gram, 0.92 mmol) in 5.11 grams (54.9 mmol) of aniline was added to the flask using a syringe pump (model 341A, Sage Instruments) over a period of 35 minutes with stirring. The reaction was stopped five minutes after completion of the addition.
[b]The K-OMS-2 was prepared by adding 11.57 grams (58.5 mmol) of MnCl$_2$.4H$_2$O and 34 mL of double distilled water (DDW) to a flask (Solution A). KMnO$_4$ (6.95 grams, 44.0 mmol) was dissolved in 112.5 grams of DDW and 3.4 mL concentrated HNO$_3$ was added to it (Solution B). Solution B was added drop-wise to solution A with vigorous magnetic stirring. The resulting slurry was refluxed for 16 hours with stirring. The product was then filtered and washed several times with DDW and dried at 120° C. for 12 hours. The series of H-K-OMS-2 catalysts were exchanged the number of times indicated by adding 50 mL of 1M HNO$_3$ to 2.0 grams of K-OMS-2. The slurry was stirred vigorously at 80° C. for 6 hours. The product was filtered and washed several times with DDW. The final product was filtered and washed several times with DDW. Catalyst H-K-OMS-2 (2C) was prepared by adding 50 mL of concentrated HNO$_3$ to 2.0 grams of K-OMS-2. The slurry was stirred vigorously at 80° C. for 6 hours. The final product (H-K-OMS-2) was filtered and washed several times with DDW. This process was repeated 2 times. Both products was dried at 120° C. for 12 hours and then calcined at 280° C. for 6 hours.
[c]As determined by area % HPLC analysis using a Beckman System Gold HPLC equipped with a Zorbax column (8.0 cm × 4.5 mm) and a variable wavelength detector using a wavelength of 290 nm. The eluent was water with 0.05 M ammonium acetate and acetic acid (pH 5.0 ± 0.3) and acetonitrile.

TABLE 3

Effect of Temperature on Selectivity[a]

| Catalyst[b] | Temperature (° C.) | ortho/para ratio[c] | % ortho[d] |
|---|---|---|---|
| H-K-OMS-2 (4) | 110 | 16.2:1 | 94.2 |
| H-K-OMS-2 (4) | 120 | 10.2:1 | 91.1 |
| H-K-OMS-2 (4) | 130 | 6.6:1 | 86.8 |
| H-K-OMS-2 (4) | 140 | 5.1:1 | 83.6 |
| H-K-OMS-2 (4) | 150 | 2.8:1 | 73.7 |
| H-K-OMS-2 (4) | 160 | 2.1:1 | 67.7 |

FOOTNOTES TO TABLE 3

[a]Aniline (5.11 grams, 54.9 mmol) and 0.20 gram of the catalyst (H-K-OMS-2) were placed in a 25 mL 3-neck round bottom flask fitted with a reflux condenser, thermometer, and magnetic stirrer. The flask was purged with N$_2$ gas for an hour and heated to 110° C. PHA (0.10 gram, 0.92 mmol) in 5.11 grams (54.9 mmol) of aniline was added to the flask using a syringe pump (model 341A, Sage Instruments) over a period of 35 minutes with stirring. The reaction was stopped five minutes after completion of the addition.
[b]The K-OMS-2 was prepared by adding 11.57 grams (58.5 mmol) of MnCl$_2$.4H$_2$O and 34 mL of double distilled water (DDW) to a flask (Solution A). KMnO$_4$ (6.95 grams, 44.0 mmol) was dissolved in 112.5 grams of DDW and 3.4 mL concentrated HNO$_3$ was added to it (Solution B). Solution B was added drop-wise to solution A with vigorous stirring. The resulting slurry was refluxed for 16 hours with stirring. The product was then filtered and washed several times with DDW and dried at 120° C. for 12 hours. Catalyst H-K-OMS-2 (4) was prepared by adding 50 mL of 1 M HNO$_3$ to 2.0 grams of K-OMS-2. The slurry was stirred vigorously at 80° C. for 6 hours. The product was filtered and washed several times with DDW. This process was repeated four times. The final product was filtered and washed several times with DDW and dried at 120° C. for 12 hours and then calcined at 280° C. for 6 hours.
[c]As determined by area % HPLC analysis using a Beckman System Gold HPLC equipped with a Zorbax column (8.0 cm × 4.5 mm) and a variable wavelength detector using a wavelength of 290 nm. The eluent was water with 0.05 M ammonium acetate and acetic acid (pH 5.0 ± 0.3) and acetonitrile.
[d]Area percent o-aminodiphenylamine divided by area percent o-aminodiphenylamine plus area percent p-aminodiphenylamine.

TABLE 4

Effect of Catalyst Weight on Selectivity at 120° C.[a]

| Catalyst[b]   | Grams of Catalyst | ortho/para ratio[c] | % ortho[d] |
|---------------|-------------------|---------------------|------------|
| H-K-OMS-2 (4) | 0.20              | 2.1:1               | 67.7       |
| H-K-OMS-2 (4) | 0.30              | 10.4:1              | 91.2       |
| H-K-OMS-2 (4) | 0.40              | 10.5:1              | 91.3       |
| H-K-OMS-2 (4) | 0.50              | 10.5:1              | 91.3       |

FOOTNOTES TO TABLE 4
[a]Aniline (5.11 grams, 54.9 mmol) and 0.20 gram of the catalyst (H-K-OMS-2) were placed in a 25 mL 3-neck round bottom flask fitted with a reflux condenser, thermometer, and magnetic stirrer. The flask was purged with $N_2$ gas for an hour and heated to 120° C. PHA (0.10 gram, 0.92 mmol) in 5.11 grams (54.9 mmol) of aniline was added to the flask using a syringe pump (model 341A, Sage Instruments) over a period of 35 minutes with stirring. The reaction was stopped five minutes after completion of the addition.
[b]The K-OMS-2 was prepared by adding 11.57 grams (58.5 mmol) of $MnCl_2 \cdot 4H_2O$ and 34 mL of double distilled water (DDW) to a flask (Solution A). $KMnO_4$ (6.95 grams, 44.0 mmol) was dissolved in 112.5 grams of DDW and 3.4 mL concentrated $HNO_3$ was added to it (Solution B). Solution B was added drop-wise to solution A with vigorous magnetic stirring. The resulting slurry was refluxed for 16 hours with stirring. The product was then filtered and washed several times with DDW and dried at 120° C. for 12 hours. Catalyst H-K-OMS-2 (4) was prepared by adding 50 mL of 1 M $HNO_3$ to 2.0 grams of K-OMS-2. The slurry was stirred vigorously at 80° C. for 6 hours. The product was filtered and washed several times with DDW. This process was repeated four times. The final product was filtered and washed several times with DDW and dried at 120° C. for 12 hours and then calcined at 280° C. for 6 hours.
[c]As determined by area % HPLC analysis using a Beckman System Gold HPLC equipped with a Zorbax column (8.0 cm × 4.5 mm) and a variable wavelength detector using a wavelength of 290 nm. The eluent was water with 0.05 M ammonium acetate and acetic acid (pH 5.0 ± 0.3) and acetonitrile.
[d]Area percent o-aminodiphenylamine divided by area percent o-aminodiphenylamine plus area percent p-aminodiphenylamine.

In view of the many changes and modifications that can be made without departing from principles underlying the invention, reference should be made to the appended claims for an understanding of the scope of the protection afforded the invention.

What is claimed is:

1. A process of preparing ortho substituted phenylamines comprising contacting phenylhydroxylamine, optionally substituted with at least one inert substituent, with a nucleophilic reagent in the presence of a manganese oxide at a temperature between about 10° C. and about 170° C. and a pressure from subatmospheric to superatmospheric such that an ortho substituted phenylamine, optionally correspondingly substituted with at least one inert substituent, is formed.

2. The process of claim 1 wherein the phenylhydroxylamine is unsubstituted phenylhydroxylamine.

3. The process of claim 1 wherein the phenylhydroxylamine is substituted with at least one member selected from the group consisting of $C_1$–$C_{10}$ alkyl, $C_6$–$C_{10}$ aryl, and $C_6$–$C_{10}$ alkaryl moieties.

4. The process of claim 1 wherein the nucleophilic reagent is selected from the group consisting of ammonia, water, $C_1$–$C_{20}$ aliphatic alcohols, phenols, halides, and amines having the formula $R'_2NH$ wherein each R' may independently be a hydrogen, $C_1$–$C_{20}$ aliphatic, $C_4$–$C_8$ alicyclic, or $C_6$–$C_{15}$ aryl or alkaryl moiety.

5. The process of claim 1 wherein the nucleophilic reagent is an amine represented by the formula $R'_2NH$ wherein each R' is independently a hydrogen, $C_1$–$C_5$ alkyl, or $C_6$–$C_{10}$ phenyl or alkyl-substituted phenyl moiety.

6. The process of claim 5 wherein the nucleophilic reagent is aniline.

7. The process of claim 1 wherein the molar ratio of nucleophilic reagent to phenylhydroxylamine ranges from about 2 to about 100.

8. A process for preparing ortho substituted phenylamines comprising contracting phenylhydroxylamine, optionally substituted with at least one inert substituent, with a nucleophilic reagent, the molar ratio of nucleophilic reagent to phenylhydroxylamine ranging from about 2 to about 100, the contacting of the phenylhydroxylamine and nucleophilic reagent being conducted in the absence of oxygen and in the presence of a catalyst that is a cryptomelane-type manganese oxide Octahedral Molecular Sieve, with a composition of $KMn_8O_{16} \cdot nH_2O$ (n=0.5–10) in which said molecular sieve comprises $MnO_6$ octahedral structural units that are edge and corner shared to form a 4.6×4.6 tunnels as a result of 2×2 arrangement of octahedra, in which the potassium ions are present in the tunnels with water and said potassium ions are ion-exchanged by $H^+$ ions using nitric acid to obtain the acidic form of said sieve at temperatures ranging from about 70° C. to about 120° C., whereby an optionally-substituted ortho substituted phenylamine is formed.

9. The process of claim 8 wherein the phenylhydroxylamine is unsubstituted phenylhydroxylamine.

10. The process of claim 8 wherein the nucleophilic reagent is selected from the group consisting of ammonia, water, $C_1$–$C_{20}$ aliphatic alcohols, phenols, halides, and amines having the formula $R'_2NH$ wherein each R' may independently be a hydrogen, $C_1$–$C_{20}$ aliphatic, $C_4$–$C_8$ alicyclic, or $C_6$–$C_{15}$ aryl or alkaryl moiety.

11. The process of claim 8 wherein the nucleophilic reagent is aniline.

12. The process of claim 8 wherein the ortho substituted phenylamine is represented by the formula:

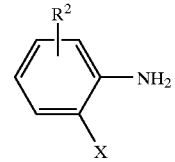

wherein $R^2$ is hydrogen or at least one $C_1$–$C_{10}$ alkyl moiety, and X is selected from hydroxy, halo, $C_1$–$C_{20}$ alkoxy, phenoxy, and amino of the formula —$NR'_2$ wherein each R' is independently a $C_1$–$C_{20}$ aliphatic, $C_4$–$C_8$ alicyclic, or $C_6$–$C_{15}$ aryl or alkaryl moiety.

13. The process of claim 12 wherein X is amino and the ortho substituted phenylamine is a o-phenylenediamine.

14. The process of claim 13 wherein the ortho substituted phenylamine is o-aminodiphenylamine represented by the formula:

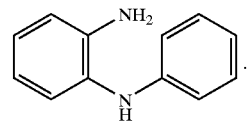

* * * * *